United States Patent [19]

N'Guyen et al.

[11] Patent Number: 5,352,438
[45] Date of Patent: Oct. 4, 1994

[54] ANTI-FREE RADICAL TOPICAL COMPOSITION BASED ON DISMUTASE SUPEROXIDE AND A PHOSPHONIC DERIVATIVE

[75] Inventors: Quang L. N'Guyen, Antony; Jean-Baptiste Galey, Paris, both of France

[73] Assignee: L'Oreal, Paris, France

[21] Appl. No.: 962,597

[22] PCT Filed: Apr. 30, 1992

[86] PCT No.: PCT/FR92/00400

§ 371 Date: Jan. 26, 1993

§ 102(e) Date: Jan. 26, 1993

[87] PCT Pub. No.: WO92/19224

PCT Pub. Date: Nov. 12, 1992

[30] Foreign Application Priority Data

May 3, 1991 [FR] France ................... 9105464

[51] Int. Cl.⁵ ................... A61K 37/48; A61K 7/00
[52] U.S. Cl. ................... 424/45; 424/94.1; 424/94.4; 424/401; 514/836; 514/844
[58] Field of Search ............... 424/401, 45, 94.1, 94.4, 424/78.03; 514/836, 844

[56] References Cited

U.S. PATENT DOCUMENTS

| | | | |
|---|---|---|---|
| 4,129,644 | 12/1978 | Kalopissis et al. | 424/94.4 |
| 4,784,790 | 11/1988 | Disch et al. | 252/174.12 |
| 4,957,740 | 9/1990 | Wilder | 424/94.4 |
| 5,114,716 | 5/1992 | N'Guyen et al. | 424/401 |
| 5,169,630 | 12/1992 | Okaya et al. | 424/401 |

FOREIGN PATENT DOCUMENTS 0193925 9/1986 European Pat. Off. .
0273579 7/1988 European Pat. Off. .
01250304A 10/1989 Japan .

OTHER PUBLICATIONS

Eur. J. Rheumatal and Inflammation, 4, pp. 173–182, 1982, "Orgotein-(Bovine Cu–Zn Superoxide Dismutase), An Anti-Inflammatory Protein Drug: Discovery, Toxicology and Pharmacology", pp. 173–182.

International Conference on Medical, Biochemical and Chemical Aspects of Free Radicals, Apr. 9–13, 1982, Morimoto et al., "Preparation of Polyoxyethylene-Modified Superoxide Dismutase", p. 317.

New Trends in Allergy II, ed. Ring et al., Springe-Verlag, "Superoxide Dismutase: Rationale of Therapeutic Use, Established Clinical Effects, and Perspectives", 1986, pp. 325–534.

International Conference on Medical, Biochemical and Chemical Aspects of Free Radicals, Apr. 9–13, 1988, Ando et al., "Synthesis of SOD Derivatives Which Bind to Biomembrane Surface", p. 318.

Primary Examiner—Thurman K. Page
Assistant Examiner—Robert H. Harrison
Attorney, Agent, or Firm—Cushman, Darby & Cushman

[57] ABSTRACT

Cosmetic or pharmaceutical composition containing a dismutase superoxide (DSO) in combination with a phosphonic acid derivative used as metal chelating agent. These compositions are used in topical administration, in particular in the fight against skin aging and in the protection of the skin against radiation exposure.

11 Claims, No Drawings

ANTI-FREE RADICAL TOPICAL COMPOSITION BASED ON DISMUTASE SUPEROXIDE AND A PHOSPHONIC DERIVATIVE

The present invention has as its goal cosmetic or pharmaceutical compositions containing a dismutase superoxide (DSO) in combination with derivatives of phosphonic acid used as a metal chelating agent.

These compositions are applied topically, in particular in the fight against skin aging and in protecting skin against radiation exposure.

It is known that dismutase superoxides are enzymes capable of inducing the dismutation of superoxide ions, in accordance with the reaction:

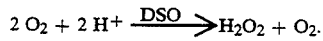

$$2\,O_2^- + 2\,H^+ \xrightarrow{DSO} H_2O_2 + O_2.$$

Dismutase superoxides extracted from cow erythrocytes (Markovitz, J. BIOL. CHEM., 234, p. 40, 1959) and from *Escherichia coli* (Keele and Fridovich, J. BIOL. CHEM., 245, p. 6176, 1970) have been previously described.

Both dismutase superoxides extracted from marine bacterial strains and the procedure used for their preparation are described in French Patent Application No. 73,13670, filed on Apr. 16, 1973.

Dismutase superoxides make it possible, in particular, to protect the skin and hair, while preserving intact the natural keratinous structure, as described, for example, in French Patent Application No. 75,31354. The protection thus afforded may be due to the inhibition of keratin-oxidation phenomena. The dismutase superoxides enhance cutaneous cellular respiration and preserve, or improve, skin qualities, i.e., softness to the touch, suppleness, and elasticity. The presence of these superoxides in hair compositions also allows preservation or enhancement of scalp quality, while at the same time protecting the skin on the hands of the person applying these compositions.

Furthermore, dismutase superoxides protect the skin against inflammatory phenomena caused by ultra-violet radiation, and against skin aging resulting from this same stimulus.

By means of these various properties, dismutase superoxides can be used in cosmetic preparations for skin or hair, as well as in pharmaceutical compounds used dermatologically or ophthalmologically.

In fact, the superoxide ion $O_2^-$ (active oxygen) is a free radical whose instability and reactivity in the case of an organism make it a toxic compound, since, in the presence of metal ions, it produces highly-toxic hydroxyl radicals (OH).

The DSO produces a protective effect, by trapping the superoxide ions. It thus forms a biological defense system against the toxic effects of oxygen.

It was revealed that the chelating agents, and thus the metal inactivating agents, may, in some cases, attenuate production of the toxic OH radicals.

It has now been found, in an entirely unexpectedly, surprising way, that not all of the metal chelating agents are suitable, since some of them are, moreover, agents which activate radical reactions, and thus act to oppose the suppression of formation of these free radicals.

Therefore, the present invention has, as its goals, an anti-radical composition characterized by the fact that it comprises the dismutase superoxide in combination with at least one of a special selection of metal chelating agents, especially the derivatives of phosphonic acid, preferably polyphosphonic derivatives, which do not simultaneously stimulate the formation of free radicals. To the contrary, these derivatives reinforce synergistically the protective action exerted by the DSO.

Most especially, the invention has as its aim a cosmetic composition intended for topical use, characterized by the fact that this composition contains at least one dismutase superoxide in combination with at least one phosphonic derivative used as metal chelating agent.

The aforementioned synergistic effect between the DSO and the phosphonic compound is especially pronounced when the weighted ratio of DSO to the phosphonic compound(s) ranges between 2 and 25, and preferably between 10 and 25.

The term "DSO" signifies any constituent producing a dismutase superoxide action, i.e., any enzyme capable of catalyzing the dismutation reaction mentioned previously, as well as any product producing this activity, these products forming a group including, in particular, DSO's modified by grafting with polyalkylene oxide, polyethyleneglycol, polysaccharide, or acylated groups, as well as substances containing these products. In this regard, mention may be made of European Patent Application No. EP 223,257.

The DSO used according to the invention may also be DSO as modified, in particular, based on information extracted from the article of H. Morimoto, "International Conference on Medical, Biochemical and Chemical Aspects of Free Radicals" (April, p. 9–13, 1988, Kyoto), p. 317, or from Mr. Ando Yukio, p. 318 (same source), or, yet again, from JP No. 01250304 (Kanebo).

The DSO used according to the invention may, moreover, be used in a stabilized form using conventional methods, e.g., the phosphate technique, in the presence of alkaline metal chloride and saccharose, such as those published in French application Patent No. 2,634,125 (Nippon).

All of the dismutase superoxides described above, as well as the variants and equivalents which the specialist can infer based on this literature, are suitable for use as DSO according to the invention.

DSO's that can be used according to the invention may have various origins.

In particular, DSO's of animal (e.g., cow, pig, etc.), human (e.g., placenta, blood), bacterial, yeast, vegetable (e.g., fungi, algae, spinach, etc.), or biotechnological origin (e.g., genetic engineering) can be mentioned.

As examples of cow DSO, mention may be made, in particular, of the Cu-Zn type of DSO, which has been purified until homogeneity is achieved and approved for clinical applications ("New Trends in Allergy," I. Ring et al., Ed. Springer Verlag, 1986).

As examples of biotechnological DSO's obtained, in particular, from cultures of bacteria, yeasts, animal cells, etc., the recombinant human Cu-Zn DSO made by UBE Industries, Ltd., may be cited.

Among examples of bacteria-derived DSO's, mention may be made, in particular, of those extracted from *Escherichia coli;* among the dismutase superoxides extracted from fungi, those derived from *Pleurotus olearius;* and, among the dismutase superoxides of blood, the eythrocupreines.

Mention may also be made of dismutase superoxides extracted from marine bacterial strains, such as *Photo-*

*bacterium phosphoreum, Photobacterium leiognathi,* or *photobacterium sepia,* for example.

Among the various strains which can be used, mention may be made of the following strains: *Photobacterium phosphoreum* No. ATCC 11040, *Photobacterium leiognathi* No. ATCC 25521, *Photobacterium sepia* No. ATCC 15709, *Escherichia coli* No. ATCC 15224, and *Pleurotus olearius* Gillet (Cryptogamy Laboratory of Paris).

The DSO's used according to the invention may be prepared by implementing the methods previously described in the article of KEELE et al, and in EUR. J. RHEUMATOL AND INFLAMMATION, 4, 173–182 (1982).

Dismutase superoxides extracted from marine bacterial strains may be prepared using the procedure described in French Patent Application No. 73,13670, cited above.

Several types of DSO's can be used in accordance with the invention, i.e., DSO's containing iron, manganese, and copper-zinc; the latter is preferred.

The metal chelating agents which can be used according to the invention are compounds whose molecule contains at least one phosphonic function, and, preferably, those which contain several of these functions.

Polyphosphonic derivatives of this kind are preferably selected from among ethylenediamine tetra(methylene phosphonic) acid, hexamethylene diamine tetra (methylene phosphonic) acid, diethylenetriamine penta (methylene phosphonic) acid, 1-hydroxy-ethylidene 1,1-diphosphonic acid, aminotri(methylene phosphonic) acid, and their salts, in particular, ammonium and alkaline metal salts.

The polyphosphonic derivatives which may be used in an especially preferable manner according to the invention are, in particular, ethylenediamine tetra (methylene phosphonic) acid, diethylene triamine penta (methylene phosphonic) acid, and their sodium salt. These compounds can be used, in particular, in their commercialized forms under the names DEQUEST 2041, 2046, 2061, and 2066, marketed by Monsanto.

Because the binary anti-free radical combination according to the invention is used mainly in cosmetic preparations designed to fight skin aging and to protect the skin and hair against radiation exposure, the invention thus also has as its aim these cosmetic and dermatological compositions.

In the topical preparations according to the invention, DSO generally represents from 0.001 to 4% by weight, and preferably from 0.75 to 1.7%. The phosphonic acid derivative is normally present in a proportion of from 0,005% to 2% by weight, and preferably from 0.05% to 0.1% by weight.

The preparations according to the invention, intended for topical application, are, in particular, lotion- or serum-type solutions or dispersions, milk-type emulsions having a liquid or semi-liquid consistency and obtained by dispersion of a fatty or aqueous phase (O/W), or reversed (W/E), cream- or gel-type emulsions having a soft consistency, or ionic or non-ionic microspheres, microgranulates, or vesicular dispersions.

These compositions are conventionally prepared. They produce, most notably, cleansing, protection, or skin-care creams for the face, hands, or body (e.g., day or night creams, make-up removal creams, make-up foundation creams, and sun-screen creams), fluid make-up foundations, make-up removal milks, protective or skin-care body milks, sun-protection lotions, artificial tanning lotions, bath preparations, or deodorizing preparations containing a bactericidal agent.

The compositions according to the invention may also contain solid preparations forming soaps or cleansing cakes.

Compositions of a liquid type can be produced as aerosol sprays containing, in addition, a pressurized propulsive agent.

Skin preparations according to the invention contain, in addition to the binary combination according to the invention, active ingredients or excipients conventionally used in the aforementioned formulations, such as surfactants, coloring agents, perfumes, preservatives, emulsifiers, liquid vehicles such as water, fatty substances such as natural or synthetic oils designed to make up the fatty phase of milks or creams, resins, etc. The compounds intended to form a fatty phase include, for example, mineral, animal, vegetable, or synthetic oils, waxes, fatty alcohols, or fatty acids.

The group of mineral oils includes vaseline oil and the group of synthetic oils, ethyl and isopropyl palmitates, alkyl myristates such as isopropyl, butyl, and cetyl myristate, hexyl stearate, the triglycerides of octanoic and decanoic acids (e.g., the product sold under the tradename MIGLYOL by the Dynamit-Nobel Company), cetyl ricinoleate, stearyl octanoate (purcellin oil) and hydroxylated polyisobutene octanoate.

The group of vegetable oils includes, for example, sweet almond, avocado, coconut, wheat germ, corn, ricin, olive, palm, sesame, soy, argan, onager, and borage oils, essential oils, and vegetable waxes such as beeswax, and synthetic waxes.

The group of fatty alcohols includes cetylic, stearylic, myristic, hydroxystearylic, oleic, isostearylic, laurylic, hexadecylic, ricinoleylic, behenylic, and erucylic alcohol, as well as 2-octyldodecanol.

The fatty acid group includes stearic, myristic, palmitic, oleic, linoleic, lauric, isostearic, hydroxystearic, linolenic, ricinoleic, arachidic, behenic, and erucic acid, and the lanolinic acids.

Hair preparations according to the invention may be produced as aqueous, alcoholic, or hydroalcoholic solutions, or as creams, gels, emulsions, foams, or as aerosol sprays also containing a pressurized propulsive agent.

In addition to conventional active ingredients, they may contain various additives normally present in these hair preparations, such as liquid vehicles, or which exist in the form of gels, perfumes, coloring agents, preservatives, thickening agents, etc.

They exist, for example, as skin-care creams, lotions, gels, serums, or foams, shampoos, hair-setting lotions, treatment lotions, hairdressing creams or gels, dyeing preparations (in particular, oxidation dyeing agents) potentially in the form of coloring shampoos, restructuring agents, permanent preparations (especially preparations for the first stage of permanents), lotions or gels for prevention of hair loss, etc.

The preparations according to the invention include, for example:

shampoos containing, in addition to a dismutase superoxide and the polyphosphonic derivative, an alkaline detergent, whether anionic or non-ionic;

dyeing preparations, include coloring shampoos, which contain coloring agents or coloring precursors such as those mentioned above, e.g., m-diaminoanisole, o-, m-, or p-aminophenol, nitroparaphenylenediamine, paraphenylene-diamine, p-toluenediamine, 5,6-dihydroxy indole sulfate, etc.;

preparations for the first phase (reduction phase) of a permanent deformation of the hair, which contain reducing derivatives such as mercaptans, sulfites, etc.;

preparations for slowing hair loss and to promote the regrowth of hair, which contain compounds such as "Minoxidil" (2,3-diamino-6-piperidino-pyrimidine-3-oxide) and its derivatives, Diazoxide (7-chloro-3-methyl-1,2,4-benzothiadiazine 1,1-dioxide), and "Phenytoin" (5,5-diphenyl imidazolidine 2,4-diketone).

It should be pointed out that the cosmetic preparations according to the invention include both preparations ready for use and concentrates which have to be diluted before use. The latter include, for example, shampoos and bath preparations.

The preparations according to the invention contain DSO and the phosphonic derivative, used either as main active ingredient or as agent protecting against oxidation of the other ingredients.

When the oxidizable ingredient to be protected undergoes accelerated decomposition in the presence of keratin fibers and/or the skin, the DSO and phosphonic derivative may be kept by themselves in dilute or concentrated aqueous solution, or as complex compounds or lyophilizates. They can be added to the other ingredients in the preparation at the moment of use.

Similarly, when the DSO and phosphonic derivative are used so as to preserve or improve skin or hair properties, these substances can be added to the composition only at the moment of use.

The preparations according to the invention may thus exist as a multi-component package containing, first, the DSO and phosphonic derivative and second, the other ingredients of the preparation. As indicated above, the DSO and phosphonic derivative may, for example, be kept in aqueous solution or as complex compounds or lyophilizates.

Moreover, the present invention is also intended to provide a cosmetic treatment characterized by the fact that a preparation containing at least one DSO in combination with at least one phosphonic derivative is applied to the hair or skin.

The cosmetic treatment process according to the invention can be implemented by using hygienic or cosmetic preparations such as those specified above, employing the normal method used for these preparations. For example: application of creams, gels, serums, lotions, make-up removal milks, or sunscreens to the skin or hair, application of a hair lotion to wet hair, shampoos, etc.

The cosmetic treatment procedure according to the invention is implemented so as to apply an efficacious quantity of DSO and phosphonic derivative, i.e., to apply a quantity sufficient to produce the desired protective effect.

This cosmetic treatment procedure is designed either to preserve the keratin structure of the skin or hair, or to preserve or enhance skin properties (softness, suppleness, elasticity), or to protect the skin against the harmful effects of ultraviolet rays.

RESEARCH STUDY

The strengthening of the properties of DSO by means of derivatives of phosphonic acid as stipulated by the invention was compared to another type of metal chelating agent, i.e., EDTA (ethylene diamine tetracetic acid). It was revealed in vitro using a method for assessing the trapping of free radicals, based on the measurement of ethylene formation.

This method consists in using chromatography to measure, in the gaseous phase, the ethylene formed from oxidation of methionine by means of the hydroxyl radical.

The working method consisted in mixing, in a head space flask, the active ingredient to be studied with the oxidizing "stress" (ascorbic acid and copper sulfate) which produced the reduced types of oxygen ($O_2$, $H_2O_2$, OH) and with the marker, i.e., methionine. The medium was incubated for one hour at 37° C. Next, the measurement of the quantity of ethylene produced was assessed using chromatography in the gaseous phase.

The EDTA was studied alone and in combination with the DSO, in the same way as a phosphonic derivative according to the invention, i.e., ethylenediamine tetra (methylene phosphonic) acid, called below DEQUEST 2041, the tradename of the product marketed by Monsanto.

The ethylene thus formed was then quantified using chromatography in the gaseous phase, by taking samples of air inside the cell. The height of the chromatogram peak obtained thus corresponded to the quantity of ethylene produced. The maximum height obtained in the absence of the active ingredient represented a 0% inhibition.

The results obtained for DEQUEST 2041 are given in Table 1, and the EDTA results, in Table 2.

TABLE 1

| | (DEQUEST) | |
| --- | --- | --- |
| DSO mg/ml | DEQUEST 2041 (mg/ml of an 88% solution | PERCENTAGE OF INHIBITION radical |
| — | — | 0 |
| 0.05 | — | 35.6 |
| — | 0.0035 | 20.8 |
| 0.025 | 0.00175 | 57.9 |

It will thus be noted that the simultaneous use of DSO and DEQUEST 2041 at a total active substance concentration substantially less than 0.05 mg/ml allows radical inhibition much greater than that obtained for DSO alone at a concentration of 0.05 mg/ml, thereby revealing a synergetic inhibition of the generation of free radicals.

TABLE 2

| | (EDTA) | |
| --- | --- | --- |
| DSO mg/ml | EDTA (mg/ml of an 88% solution | PERCENTAGE OF INHIBITION radical |
| — | — | 0 |
| 0.05 | — | 35.6 |
| — | 0.0035 | −0.04 |
| 0.025 | 0.00175 | 7.0 |

It will thus be seen that the simultaneous use of DSO and EDTA causes a 7% rate of inhibition of free radicals. This inhibition rate is, therefore, less than that obtained using DSO alone, which does not demonstrate the synergy effect.

Several examples of cosmetic preparations according to the invention will now be provided as non-restrictive illustrations.

EXAMPLE 1: O/W Emulsion

| | % by weight |
|---|---|
| DSO Cu—Zn (M.A.) | 0.08 |
| Ethylenediamine tetra(methylene phosphonic acid) (DEQUEST 2041) (M.A.) | 0.005 (11 μmoles) |
| Oxyethylenated polyethylene glycol 50 | 1.5 |
| Monodiglyceryl stearate | 1.5 |
| Vaseline oil | 24 |
| Cetylic alcohol | 2.5 |
| Triethanolamine q.s. pH = 7 | |
| Water q.s.p. | 100 |

EXAMPLE 2: O/W Emulsion

| | % by weight |
|---|---|
| DSO-Mn (A.M.) | 0.026 |
| Pentasodic salt of ethylenediamine tetra(methylene phosphonic) acid (DEQUEST 2046) (A.M.) | 0.013 (24 μmoles) |
| Polyglyceryl sesquiisostearate | 4.0 |
| White beewax | 0.5 |
| Magnesium stearate | 1.5 |
| Aluminum stearate | 1 |
| Hydrogenated ricin oil oxyethylenated using 7 moles of ethylene oxide | 3 |
| Isopropyl palmitate | 10 |
| Perhydrosqualene | 15 |
| Water q.s.p. | 100 |

EXAMPLE 3: O/W Emulsion

| | % by weight |
|---|---|
| DSO Cu—Zn (M.A.) | 1 |
| Heptasodic salt of diethylene triamine penta (methylene phosphonic) acid (DEQUEST 2066) (M.A.) | 0.1 (50 μmoles) |
| Cetearylic ether of polyethylene glycol | 5 |
| Cetylic alcohol | 1 |
| Glyceryl stearate | 1 |
| Vaseline oil | 6 |
| Isopropyl myristate | 3 |
| Dimethicone | 1 |
| Glycerine | 5 |
| Methyl parahydroxybenzoate | 0.3 |
| Water qsp | 100 |

EXAMPLE 4: SERUM

| | % by weight |
|---|---|
| Epikuron 200 soy lecithin (sold by the Lucas Meyer Company) | 0.75 |
| Cholesterol | 0.20 |
| HS21 sodium acylglutamate (sold by the AJINOMOTO Company) | 0.05 |
| Glycerine | 1 |
| DSO Cu—Zn (A.M.) | 0.04 |
| Ethylenediamine tetra-(methylene phosphonic) (DEQUEST 2041) | 0.008 (18 μmoles) |
| Methyl parahydroxybenzoate | 0.2 |
| Mixture of carboxyvinyl acids "CARBOPOL 940" (sold by Goodrich) | 0.1 |
| Triethnaolamine qs pH = 7 | |
| Water qsp | 100 |

EXAMPLE 5: Vesicular Dispersion

| | % by weight |
|---|---|
| Non-ionic amphipile* | 0.9 |
| HS21 sodium acylglutamate | 0.1 |
| (sold by the Ajinomoto Company) | |
| Glycerine | 3.00 |
| DSO Cu—Zn (A.M.) | 0.08 |
| Ethylenediamine tetra-(methylene phosphonic acid) (DEQUEST 2041) | 0.005 (11 μmoles) |
| Perhydrosqualene | 10 |
| Methyl perhydroxybenzoate | 0.2 |
| Mixture of carboxyvinyl acids "CARBOPOL 940" (sold by Goodrich) | 0.4 |
| Triethanolamine s pH = 7 | |
| Water qsp | 100 |

*The non-ionic amphipile has the following formula:
$$C_{12}H_{25}-[OC_2H_3(R)]-O-C_3H_5(OH)-O]_n-H$$
where $-OC_2H_3(R)-$ is formed by a mixture of the radicals:
$$-O-CH-CH_2- \text{ and } -O-CH_2-CH-;$$
$$\phantom{-O-CH-CH_2-}R \phantom{\text{ and } -O-CH_2-CH-}R$$
where $-C_3H_5(OH)-O-$ is formed by a mixture of radicals:
$$CH_2-CH-O- \text{ and } -CH-CH_2-O-;$$
$$\phantom{CH_2-}CH_2OH \phantom{\text{ and } -CH-}CH_2OH$$
where n = 6
and where R is a mixture of the radicals $C_{14}H_{29}$ and $C_{16}H_{33}$.

EXAMPLE 6: Anti-Hair Loss gel

| | % by weight |
|---|---|
| DSO Cu—Zn (A.M.) | 0.05 |
| Pentasodic salt of ethylenediamine tetra-(methylene phosphonic acid) (DEQUEST (2046) | 0.07 (129 μmoles) |
| Propylene glycol | 5 |
| "CARBOPOL 934" (mixture of carboxyvinyl acids) | 0.5 |
| Minoxidil (see above) | 1 |
| Triethanolamine qs pH = 7 | |
| Preservatives qs | |
| Water qsp | 100 |

EXAMPLE 7: Sunscreen Milk

| | % by weight |
|---|---|
| Cetylstearylic alcohol | 2.6 |
| 330E oxyethylenated cetylstearylic alcohol | 0.6 |
| Vaseline oil | 6 |
| Isopropyl myristate | 3 |
| Stearylic alcohol | 2.5 |
| Ditertiobutyl-4-hydroxytoluene | 0.025 |
| Paramethyl benzylidene camphor | 2.5 |
| 2-ethylhexyl P-methoxycinnamate | 4 |
| Glycerol | 1.2 |
| DSO Cu—Zn | 0.2 |
| Pentasodic salt of ethylenediamine tetra-(methylene phosphonic acid) (DEQUEST (2046) | 0.015 (28 μmoles) |
| Preservatives qs | |
| Perfumes qs | |
| Water qsp | 100 |

We claim:

1. A cosmetic or pharmaceutical composition for topical application to the hair or skin comprising 0.001 to 4 percent by weight of at least one dismutase superoxide in combination with 0.005 to 2 percent by weight of at least one polyphosphonic acid or salt thereof, said polyphosphonic acid being selected from the group consisting of ethylenediamine tetra(methylene phosphonic) acid, hexamethylene diamine tetra(methylene phosphonic) acid, diethylenetriamine penta(methylene phosphonic) acid, 1-hydroxyethylidene 1,1-diphosphonic acid, aminotri(methylene phosphonic) acid and a salt thereof.

2. Composition according to claim 1 wherein the weight ratio of said dismutase superoxide to said polyphosphonic acid or salt thereof ranges from 25/1 to 2/1.

3. The composition of claim 1 wherein said dismutase superoxide is present in an amount ranging from 0.75 to 1.7 percent by weight based on the total weight of said composition.

4. The composition of claim 1 wherein said polyphosphonic acid is present in an amount ranging from 0.05 to 0.1 percent by weight based on the total weight of said composition.

5. The composition of claim 1 wherein said dismutase superoxide is of animal, bacterial, yeast, vegetable, marine or biotechnology origin.

6. The composition of claim 1 wherein said dismutase superoxide contains iron, manganese or copper-zinc.

7. The composition of claim 1 wherein said salt is selected from the group consisting of an ammonium salt and an alkaline metal salt.

8. The composition of claim 7 wherein said alkaline metal salt is sodium salt.

9. The composition of claim 1 in the form of a lotion, an emulsion, a milk, microspheres, microgranulates, a cream, a gel, a salve, an aerosol spray, ionic vesicles or non-ionic vesicles.

10. The composition of claim 1 which also contains a surfactant, a coloring agent, a perfume, a preservative, an emulsifier, a resin or a wax.

11. A method for the treatment of the skin to combat skin aging or for the protection of the skin and hair against radiation exposure, said method comprising topically applying to the skin or hair, or both, in an amount effective for said treatment, a composition comprising 0.001 to 4 percent by weight of at least one dismutase superoxide in combination with 0.005 to 2 percent by weight of at least one polyphosphonic acid or a salt thereof, said polyphosphonic acid being selected from the group consisting of ethylenediamine tetra(methylene phosphonic) acid, hexamethylenediamine tetra(methylene phosphonic) acid, diethylenetriamine penta(methylene phosphonic) acid, 1-hydroxyethylidene 1,1-diphosphonic acid, aminotri(methylene phosphonic) acid and a salt thereof.

* * * * *